US007416749B2

(12) United States Patent
Huang et al.

(10) Patent No.: US 7,416,749 B2
(45) Date of Patent: Aug. 26, 2008

(54) DIETARY SUPPLEMENT AND RELATED METHOD

(75) Inventors: Ruo Huang, Long Beach, CA (US); Audra J. Davies, Long Beach, CA (US); Aaron W. Crawford, Los Angeles, CA (US); Edward S. Kahler, Anaheim, CA (US); Donald J. Pusateri, Hemet, CA (US); Stephen R. Missler, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 355 days.

(21) Appl. No.: 10/915,784

(22) Filed: Aug. 11, 2004

(65) Prior Publication Data
US 2005/0244518 A1 Nov. 3, 2005

Related U.S. Application Data

(63) Continuation-in-part of application No. 10/360,789, filed on May 7, 2002, now Pat. No. 6,989,161, which is a continuation-in-part of application No. 09/878,377, filed on Jun. 12, 2001, now Pat. No. 6,511,675.

(60) Provisional application No. 60/210,746, filed on Jun. 12, 2000.

(51) Int. Cl.
*A61K 36/00* (2006.01)
*A61K 36/53* (2006.01)
*A01K 36/31* (2006.01)

(52) U.S. Cl. .................. 424/736; 424/725; 424/745; 424/755; 424/777

(58) Field of Classification Search ............. 424/725, 424/736
See application file for complete search history.

(56) References Cited

U.S. PATENT DOCUMENTS

| 4,115,552 | A | * | 9/1978 | Hamill et al. ............. 424/118 |
| 5,091,195 | A | * | 2/1992 | Havens ...................... 426/2 |
| 5,356,636 | A | | 10/1994 | Schneider et al. |
| 5,401,502 | A | | 3/1995 | Wunderlich et al. |
| 5,514,382 | A | | 5/1996 | Sultenfuss |
| 5,578,336 | A | | 11/1996 | Monte |
| 5,612,039 | A | | 3/1997 | Policappelli et al. |
| 5,654,011 | A | | 8/1997 | Jackson et al. |
| 5,686,108 | A | | 11/1997 | Pusateri et al. |
| 5,770,217 | A | | 6/1998 | Kutilek, III et al. |
| 5,807,586 | A | | 9/1998 | Jackson et al. |
| 5,830,887 | A | | 11/1998 | Kelly |
| 5,840,278 | A | | 11/1998 | Coleman |
| 5,882,646 | A | | 3/1999 | Pusateri et al. |
| 5,904,924 | A | | 5/1999 | Gaynor et al. |
| 5,948,443 | A | | 9/1999 | Riley et al. |
| 5,955,102 | A | | 9/1999 | Gorenbein et al. |
| 5,972,985 | A | | 10/1999 | Thomas et al. |
| 5,976,548 | A | | 11/1999 | Hsia et al. |
| 5,976,568 | A | | 11/1999 | Riley |
| 5,985,338 | A | | 11/1999 | Suh et al. |
| 6,022,901 | A | | 2/2000 | Goodman |
| 6,087,391 | A | * | 7/2000 | Weidner .................... 514/458 |
| 6,129,924 | A | * | 10/2000 | Maurel et al. ............. 424/400 |
| 6,203,818 | B1 | | 3/2001 | Vester |
| 6,231,866 | B1 | | 5/2001 | Mann |
| 6,238,672 | B1 | * | 5/2001 | Chen ......................... 424/728 |
| 6,261,598 | B1 | | 7/2001 | Runge et al. |
| 6,361,807 | B1 | * | 3/2002 | Aviram et al. ............. 424/744 |
| 6,375,993 | B1 | * | 4/2002 | Aviram et al. ............. 424/744 |
| 6,440,410 | B1 | | 8/2002 | Yegorova |
| 6,440,467 | B2 | | 8/2002 | Mann |
| 6,447,809 | B1 | * | 9/2002 | Krumhar et al. ............ 424/602 |
| 6,551,628 | B1 | | 4/2003 | Watson et al. |
| 6,579,544 | B1 | * | 6/2003 | Rosenberg et al. ......... 424/736 |
| 6,582,721 | B1 | * | 6/2003 | Lang ........................ 424/439 |
| 6,586,018 | B1 | | 7/2003 | Fasano |
| 6,638,545 | B1 | | 10/2003 | Rombi |
| 6,676,978 | B1 | | 1/2004 | Nair |

(Continued)

FOREIGN PATENT DOCUMENTS

DE 1997-000655 * 11/1996

(Continued)

OTHER PUBLICATIONS

Ebringer A, et al, Rheumatoid arthritis: proposal for the use of antimicrobial therapy in early cases, Scand J Rheumatol, 32(1):2-11 (2003) (abstract only).

(Continued)

*Primary Examiner*—Christopher R Tate
*Assistant Examiner*—Randall Winston
(74) *Attorney, Agent, or Firm*—Warner Norcross & Judd LLP

(57) ABSTRACT

A dietary supplement including a unique combination of fruits, vegetables, herbs, and optionally vitamins, minerals and specialty ingredients. The supplement can include a fruit ingredient, a vegetable ingredient and an herbal ingredient, wherein the fruit ingredient is at least one of pomegranate and citrus bioflavonoids, wherein the vegetable ingredient is at least one of asparagus, lutein, lycopene and watercress, and wherein the herbal ingredient is at least one of basil, oregano and rosemary. The supplement can be administered to subjects to correct a dietary deficiency of phytochemicals and other nutrients, improve the amount of antioxidants in the subject, and decrease free radical damage in the subject.

8 Claims, No Drawings

U.S. PATENT DOCUMENTS

| | | | |
|---|---|---|---|
| 2001/0012525 A1 | 8/2001 | Mann |
| 2002/0044980 A1 | 4/2002 | Castelli et al. |
| 2002/0119173 A1 | 8/2002 | Lin et al. |
| 2002/0168429 A1 | 11/2002 | Mann |
| 2002/0192314 A1 | 12/2002 | Cho et al. |
| 2003/0049335 A1 | 3/2003 | Stier et al. |
| 2003/0108627 A1 | 6/2003 | Selzer et al. |
| 2003/0162297 A1 | 8/2003 | Ou et al. |
| 2003/0228384 A1 | 12/2003 | Kurk et al. |
| 2004/0076692 A1 | 4/2004 | Van Norren et al. |

FOREIGN PATENT DOCUMENTS

| | | |
|---|---|---|
| EP | 0906761 | 10/1998 |
| JP | 2001-086954 | 4/2001 |
| JP | 2001-095529 | 4/2001 |
| WO | WO 0045829 | 2/1999 |
| WO | WO 0064282 | 4/2000 |
| WO | 0074697 | 12/2000 |

OTHER PUBLICATIONS

Rossi, A, et al, Protective effects of anthocyanins from blackberry in a rat model of acute lung inflammation, Free Radic Res, 37(8):891-900 (Aug. 2003) (abstract only).

Roy, S, et al, Anti-angiogenic property of edible berries, Free Radic Res, 36(9):1023-31 (Sep 2002) (abstract only).

Youdim, Ka, et al, Potential role of dietary flavonoids in reducing microvascular endothelium vulnerability to oxidative and inflammatory insults, J Nutr Biochem, 13(5):282-288 (May 2002) (abstract only).

Calucci, L, et al, Effects of gamma-irradiation on the free radical and antioxidant contents in nine aromatic herbs and spices, J Agric Food Chem, 51(4):927-34 (2003) (abstract only).

Dragland, Steinar, et al, Several culinary and medicinal herbs are important sources of dietary antioxidants, J Nutr, 133(5) 1286-90 (May 2003) (abstract only).

Kris-Etherton, Penny M, et al, Bioactive compounds in foods: their role in the prevention of cardiovascular disease and cancer, Am J Med, 113 Suppl 9B 71S-88S (Dec. 30, 2002) (abstract only).

Tan, Dx, et al, Significance of melatonin in antioxidative defense system: reactions and products, Biological Signals and Receptors, 9 (3-4) 137-59 (May-Aug. 2000) (abstract only).

Kahkonen, MP, et al, Antioxidant activity of plant extracts containing phenolic compounds, J Agr Food Chem, 47(10) 3954-62 (Oct. 1999) (abstract only).

Dragsted, Lo, et al, Dietary levels of plant phenols and other non-nutritive components: could they prevent cancer?, European J Cancer Prev, 6(6) 522-8 (Dec 1997) (abstract only).

Fejes, S, et al, Investigation of the in vitro antioxidant effect of Petroselinum crispum, Acta Pharm Hung, 68(3):150-6 (1998) (abstract only).

Logia: Back to the Garden, downloaded from http://www.logia.net/products/back_to_garden.html (Jul. 20, 2004).

* cited by examiner

DIETARY SUPPLEMENT AND RELATED METHOD

This is a continuation-in-part application of U.S. application Ser. No. 10/360,789, filed May 7, 2002, now U.S. Pat. No. 6,989,161 which is a continuation-in-part application of U.S. application Ser. No. 09/878,377, filed Jun. 12, 2001 (now U.S. Pat. No. 6,511,675), which claims benefit of U.S. Provisional Application No. 60/210,746, filed Jun. 12, 2000, all of which are hereby incorporated by reference.

BACKGROUND OF THE INVENTION

The present invention relates to a composition and method for correcting a dietary deficiency, including an inadequacy of phytochemicals, vitamins and minerals.

Many people fail to practice healthy eating habits, such as consuming an adequate quantity and variety of food to meet U.S. Recommended Dietary Allowances. Only 22% of the subjects of a National Cancer Institute Study consumed the recommended daily number of dietary servings of fruits and vegetables—despite the fact that the recommended dietary intake of fruits and vegetables is well-known. For example, *The California Daily Food Guide: Dietary Guidelines for Californians*, California Department of Health Services (1990) recommends that each person consume at least five to nine servings of fruit and vegetables per day, including one serving of a vitamin A-rich deep green or dark orange fruit or vegetable, and at least one serving of a vitamin C-rich fruit or vegetable. Additionally, it is well reported that each person should consume at least 3 servings per week of vegetable protein in the form of legumes, nuts, or seeds. Some researchers suggest that a target of 400 grams (13 ounces) of fruits and vegetables is a sensible goal for the optimal quantity to be consumed daily. In terms of variety, it is recommended that persons should eat at least three different colors of fruits and vegetables daily.

The benefits of consuming a sufficient amount and variety of fruits and vegetables are many. For example, consuming fruits and vegetables has been shown to treat and prevent a variety of degenerative diseases. In a prospective cohort study of 41,837 postmenopausal women, the association of fruit and vegetable consumption with lung cancer risk was investigated. The researchers found that the risk of lung cancer was approximately halved when the consumption of fruits and vegetables increased from 24 or less servings to an excess of 48 servings per week. Similarly, the risk of lung cancer was approximately halved when the consumption of green leafy vegetables, including spinach and parsley sources, increased from 1 or fewer servings to six or more servings per week. Steinmetz, K. et al., "Vegetables, Fruit, and Lung Cancer in the Iowa Women's Health Study," *Cancer Res*.53:536-43 (1993). Another study found that an increased intake of fresh tomatoes (a major source of lycopene) was associated with a pattern of protection for all sites of digestive tract cancer. Stahl, W. et al., "Lycopene: A Biologically Important Carotenoid for Humans?" *Arc. Biochem. Biophys*. 336:1-9 (1996).

In addition to fruits and vegetables, herbs also provide health benefits. For example, the herb, rosemary, contains antioxidants such as carnosol, which may play a preventive role in cholesterol oxidation. Likewise, the herb, basil is known for its antioxidant activity. Like fruits and vegetables, however, the dietary intake of beneficial herbs is unsatisfactory.

Further research has shown that the typical U.S. diet is lacking in phytochemicals. Phytochemicals generally refer to plant-derived compounds which, when taken daily in combination with vitamins and minerals, provide improved cardiovascular and bone health, an improved antioxidant profile, decreased free radical damage, and overall enhancement of the body's natural defense system.

The typical diet, especially the U.S. diet, includes an inadequate amount and variety of fruits, vegetables and herbs, as well as the phytochemicals and associated antioxidants present in these materials. A typical diet is similarly deficient in necessary vitamins and minerals associated with fruits and vegetables. Although conventional multivitamins can supplement western diets with needed vitamins and minerals, many of these multivitamins fail to provide phytochemicals that target free radicals in the body and thereby improve the antioxidant profile of the supplement.

SUMMARY OF THE INVENTION

The aforementioned problems are overcome in the present invention which provides a dietary supplement including a unique combination of fruits, vegetables, herbs, and optionally vitamins, minerals and specialty ingredients to correct a dietary deficiency of those materials.

The composition of the present invention provides substantial health benefits. For example, in one embodiment, it can support the health of people who consume a nutritionally deficient diet; improve antioxidant and nutrient status; replenish serum nutrient and phytochemical levels as a result of inadequate diets to levels associated with decreased risk of certain degenerative disease states; minimize free radical damage that occurs as a result of normal aging processes and exposure to environmental stresses; and/or improve the status of specific biomarkers indicative of optimal health, namely homocysteine, lipid byproducts, mineral status and glutathione peroxidase.

In a more specific embodiment, the composition of the present invention can provide $\beta$-carotene, $\alpha$-lipoic acid, selenium, and vitamins C and E, which improve the antioxidant profile of a person. Increased levels of folic acid and vitamins E target and improve cardiovascular health. Calcium, magnesium, and vitamin D targets and improves bone health. B vitamins improve energy metabolism. The compositions according to the invention can provide 100% of the U.S. Recommended Daily Intake of all vitamins and most minerals. The composition also can provide a variety of phytochemicals to produce a diverse antioxidant profile.

In an even more specific embodiment, the dietary supplement can include a combination of fruit, vegetable and herbal ingredients, wherein the fruit ingredients are selected from acerola, apple, blueberry, citrus bioflavonoids, cranberry, grape skin, plum, and pomegranate; wherein the vegetable ingredients are selected from asparagus, alfalfa, brassica, kale, lutein, lycopene, and watercress; and wherein the herbal ingredients are selected from basil, oregano, parsley, sage and rosemary. These ingredients can be concentrated, for example they may be extracted from raw ingredients. Optionally, the fruit ingredients, vegetable ingredients and herbal ingredients can be present in the composition in a ratio of about 3.5:1:1 by weight. Specialty ingredients, such as alpha lipoic acid and inositol can be added to the composition.

In yet another embodiment, the dietary supplement can include at least one fruit ingredient selected from the group consisting of citrus bioflavonoids and pomegranate, and optionally at least one of acerola, apple, blueberry, cranberry, grape skin, plum and raspberry; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

According to another aspect, there is provided a method for correcting a deficiency of nutrients, vitamins and/or phytochemicals by administering a dietary supplement to a subject, the supplement including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

In yet another aspect, there is provided a method for improving the antioxidant profile of the human body comprising administering an effective amount of a dietary supplement to a subject, the supplement comprising at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

In a fourth aspect, provided is a method for decreasing free radical damage in the human body comprising administering an effective amount of a dietary supplement including at least one fruit ingredient selected from the group consisting of citrus bioflavonoids and pomegranate, and optionally at least one of acerola, apple, blueberry, cranberry, grape skin, plum and raspberry; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

In a fifth aspect, a method is provided for enhancing the immune system of the human body comprising administering an effective amount of a dietary supplement including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

These and other objects, advantages and features of the invention will be more readily understood and appreciated by reference to the detailed description of the invention and the drawings. It is to be understood that both the foregoing general description and the following detailed description are exemplary and explanatory only and are not restrictive of the invention as claimed.

DETAILED DESCRIPTION OF THE INVENTION

I. Overview

In general, the invention relates to a dietary supplement composition comprising fruits, vegetables and herbs. In one embodiment, the composition can include a fruit ingredient, a vegetable ingredient and an herbal ingredient, wherein the fruit ingredient is at least one of pomegranate and citrus bioflavonoids, wherein the vegetable ingredient is at least one of asparagus, lutein, lycopene and watercress, and wherein the herbal ingredient is at least one of basil, oregano and rosemary.

The following fruit ingredients also can be present in the dietary supplement: acerola, apple, blueberry, cranberry, grape skin, and plum. Further, the following vegetable ingredients also can be present in the dietary supplement: alfalfa, brassica, and kale. Finally, the following herbal ingredients also can be present in the dietary supplement: sage and parsley.

The invention also relates to a method for correcting a diet-induced deficiency of fruits, vegetables and herbs, and the nutrients present in such materials. The dietary supplement of the present invention additionally can contain phytochemicals, vitamins, and minerals known to improve the body's natural defenses against oxidants, free radicals, and diseases.

II. Dietary Supplement and Method of Manufacture

The dietary supplement can include a combination of fruit, vegetable, herbal and other ingredients that provide significant health benefits. The following tables illustrate representative daily amounts of suitable fruits, vegetables, herbs, vitamins, and minerals which can be included in the supplement. The dosages can be varied as desired from application to application. For example, Dosage A represents a range of dosages of the respective ingredients that is suitable for purposes of the present invention. Dosage B represents a dosage of a particular embodiment. The unit "mg" in Tables 1-5 means that that the amount recited is given in the number of, e.g., milligrams, provided in a two-tablets per day dosage, unless otherwise noted, e.g., "IU" is recited. Thus, to determine the amount of a specific ingredient per single tablet, the amount recited in the respective tables must be halved.

TABLE 1

| Fruit Ingredient | Dosage A, mg/day | Dosage B, mg/day |
| --- | --- | --- |
| Acerola Powder | 50-500 | 300 |
| Apple extract | 25-1000 | 50 |
| Citrus Bioflavanoids | 25-1000 | 100 |
| Grape skin extract | 25-1000 | 50 |
| Plum extract | 25-1000 | 50 |
| Cranberry extract | 25-1000 | 50 |
| Pomagranate | 5-500 | 25 |
| Blueberry extract | 25-1000 | 50 |

The citrus bioflavonoids are commercially available from Access Business Group International LLC of Ada, Mich. This ingredient can be in a concentrate form, and can include naringen, hesperidin and narirutin.

TABLE 2

| Vegetable Ingredient | Dosage A, mg/day | Dosage B, mg/day |
| --- | --- | --- |
| Asparagus | 25-1000 | 50 |
| Alfalfa | 25-1000 | 70 |
| Brassica | 25-1000 | 50 |
| Kale | 20-1000 | 75 |
| Lycopene | 0.1-100 | 2 |
| Lutein esters | 0.1-100 | 2 |
| NUTRILITE Watercress | 5-500 | 28 |

NUTRILITE watercress is available from Access Business Group International LLC. The Brassica and/or kale can be in dehydrated, powdered form. As used herein the Brassica ingredient may include any material derived from plants in the Brassicae family, for example, broccoli. The lutein esters used in the supplement can be of the type sold under the name Xangold 10% beadlets, which is available from Cognis Nutrition & Health of Cincinnati, Ohio. The lycopene used in the supplement can be of the type sold under the name Lycobeads 5%, which is available from H. Reisman Corp. of Orange, N.J.

TABLE 3

| Herbal Ingredient | Dosage A, mg/day | Dosage B, mg/day |
|---|---|---|
| Basil extract | 25-1000 | 50 |
| Rosemary extract | 25-1000 | 50 |
| Sage | 5-500 | 25 |
| Oregano extract | 25-1000 | 50 |
| NUTRILITE Parsley | 5-500 | 25 |

NUTRILITE parsley is available from Access Business Group International LLC. The dietary supplement can also include ingredients in addition to the fruit, vegetable and herbal ingredients noted above. For example, suitable vitamins for use in the compositions and methods of the present invention can include, vitamin A, vitamin B1, vitamin B2, vitamin B6, vitamin B12, niacin/niacinamide, pantothenic acid, folic acid, biotin, choline, vitamin C, vitamin D, and vitamin E. Table 4 below includes a suitable vitamin profile.

TABLE 4

Vitamin Profile

| Ingredient | Dosage A, mg/day | Dosage B, mg/day |
|---|---|---|
| Vitamin C from Acerola Powder | 20-100 | 60 |
| Ascorbic Acid (C) | 100-700 | 440 |
| Vitamin A from Beta Carotene | 1000-10,000 IU | 7500 IU |
| Biotin | 0.01-4 | 0.300 |
| Pantothenic Acid from Cal Pan Gran | 5-300 | 50 |
| Choline | 10-400 | 50 |
| Folic Acid | 0.01-10 | 0.8 |
| Inositol | 5-100 | 25 |
| Vitamin E | 10-5000 IU | 150 IU |
| Mixed Tocopherols | 5-300 | 50 |
| Niacin/Niacinamide | 5-300 | 40 |
| Pyridoxine (B6) | 10-100 | 15 |
| Riboflavin (B2) | 1-100 | 12.75 |
| Thiamine (B1) | 1-100 | 11.25 |
| Vitamin A from Acetate | 100-10,000 IU | 2500 IU |
| Vitamin B12 | 0.01-50 | 0.045 |
| Vitamin D3 | 10-2000 IU | 400 IU |
| Yeast, Standardized@ (source of 100% RDA Bs) | 5-350 | 60 |

In addition to the vitamins listed above, minerals for use in the compositions and methods of the present invention include, for example, boron, calcium, chromium, copper, iodine, magnesium, manganese, molybdenum, potassium, selenium, vanadium, and zinc. Other vitamins and minerals may also be used. Table 5 below includes a mineral profile suitable for the supplement of the present invention.

TABLE 5

Mineral Profile

| Ingredient | Dosage A, mg/day | Dosage B, mg/day |
|---|---|---|
| Calcium | 100-2000 | 750 |
| Chromium | 0.01-5 | 0.120 |
| Copper | 0.01-5 | 2 |
| Iodine | 0.001-5 | 0.15 |
| Magnesium | 10-1000 | 300 |
| Manganese | 1-20 | 5 |
| Molybdenum | 0.001-75 | 0.075 |
| Potassium | 5-300 | 80 |
| Selenium | 0.001-5 | 0.100 |
| Zinc | 1-50 | 15 |

With the ingredients of Tables 1-3, and optionally the ingredients of Tables 4-5, the dietary supplement of the present invention can provide a significant portion of, and in many cases exceed, the recommended daily requirement for a variety of vitamins and minerals. Tables 6 and 7 below illustrate the potency of the dietary supplement, when taken in the above daily amounts, in terms of percentages of the daily requirements for the listed vitamins and minerals.

TABLE 6

| Vitamin | Amount/Day | % Daily Value |
|---|---|---|
| Vitamin A (75% as β-Carotene), IU | 10,000 | 200% |
| Vitamin C, mg | 500 | 833% |
| Vitamin D, IU | 400 | 100% |
| Vitamin E, IU | 150 | 500% |
| Niacin/Niacinamide, mg | 40 | 200% |
| Vitamin $B_6$, mg | 15 | 750% |
| Vitamin $B_{12}$, mcg | 45 | 750% |
| Folic Acid, mcg | 800 | 200% |
| Biotin, mcg | 300 | 100% |
| Pantothenic Acid, mg | 50 | 500% |

TABLE 7

| Minerals | Amount/Day | % Daily Value |
|---|---|---|
| Calcium, mg | 750 | 75% |
| Magnesium, mg | 300 | 75% |
| Iodine, mcg | 150 | 100% |
| Potassium, mg | 80 | 2% |
| Copper, mg | 2 | 100% |
| Zinc, mg | 15 | 100% |
| Manganese, mg | 5 | 100% |
| Chromium, mcg | 120 | 100% |
| Selenium, mcg | 100 | 143% |
| Molybdenum, mcg | 75 | 100% |

Additional specialty ingredients which can be used in the dietary supplement include, for example, methyl sulfonyl methane (MSM), α-lipoic acid (10 mg/day), catechins, polyphenols, flavanoids, lycopene, lutein, yeast, inositol, and para-aminobenzoic acid (PABA).

The dietary supplement of the present invention can be formulated using any pharmaceutically acceptable form of respective fruit concentrates, vegetable concentrates, herb concentrates, phytochemicals, vitamins, minerals, and other nutrients, including their salts. The supplements can be formulated into tablets, powders, gels, or liquids (a tablet, for the purposes of the present invention and as used throughout the application disclosure, refers to any form of a solid oral dosage, including but not limited to tablets, caplets, capsules, powders, etc.). The dietary supplements can be formulated as powders, for example, for mixing with consumable liquids such as milk, juice, water, or consumable gels or syrups for mixing into other dietary liquids or foods. The dietary supplements can also be formulated with other foods or liquids to provide pre-measured supplemental foods, for example, single-serving bars. Flavorings, binders, protein, complex carbohydrates, and the like can be added as needed.

According to one aspect of the invention, the dietary supplement is administered as three separate tablets, all three of which are administered twice a day; however, the dietary supplement may be administered in other forms and unit dosages as desired.

The dietary supplement of the present invention will be illustrated by, but is not intended to be limited to, the following examples.

EXAMPLE 1

Three tablets may be prepared to provide a) fruit, vegetable and herbal ingredients, b) vitamins and c) minerals. The first tablet includes the fruit, vegetable and herbal ingredients of Tables 1-3. The amount of each ingredient in this first tablet is half of the amount listed in the Dosage B of the Tables, as the table-listed amount is the amount present in two such tablets. The first tablet may also include carriers and other tableting aids such as silicon dioxide, magnesium oxide, calcium carbonate, croscarmellose sodium, microcrystalline cellulose and magnesium stearate in amounts that may be varied for purposes well known to those of skill in the art.

The second tablet includes vitamins of Table 4. The amount of each ingredient in this second tablet is half of the amount listed in the Table, as the table-listed amount is the amount present in two such tablets. The second tablet may also include carriers and other tableting aids such as microcrystalline cellulose, calcium carbonate, croscarmellose sodium, magnesium stearate, and silicon dioxide.

The third tablet includes minerals of Table 5. The amount of each ingredient in this third tablet is half of the amount listed in the Table, as the table-listed amount is the amount present in two such tablets. The third tablet may also include carriers and other tableting aids such as microcrystalline cellulose, calcium carbonate, croscarmellose sodium, magnesium stearate, and silicon dioxide.

The three tablets, when administered twice a day, complete the gap in phytochemicals that is present in the typical diet.

EXAMPLE 2

The following examples relate to methods of preparing the above three tablets. The ingredients are the same as those referred to above in Tables 1-5. For purposes of the following examples, however, tablets including the fruit, vegetable and herbal ingredients from Tables 1-3 are referred to as "Tablet 1"; tablets including the vitamin ingredients from Table 4 are referred to as "Tablet 2"; and tablets including the mineral ingredients from Table 5 are referred to as "Tablet 3." It is noted that other methods for preparing the tablets and other suitable delivery vehicles can be used as desired.

Tablet 1

Mixed tocopherols, D-alpha-tocopherol (succinate), and silicon dioxide (NF fine powder) are passed through a SWECO separator equipped with a 20 mesh screen into a 100 cubic foot PK blender. The ingredients are blended for ten minutes. Magnesium oxide (D.C. heavy), Acerola concentrate, citrus bioflavonoids complex, plum extract, apple extract, rosemary extract, basil extract, grape skin extract, cranberry extract, kale powder, asparagus extract, blueberry extract, parsley dehydrate, oregano extract, sage extract, pomegranate extract, and inositol are passed through a SWECO separator equipped with a 20 mesh screen into a 100 cubic foot PK blender. The ingredients are blended for ten minutes.

Lycopene (5%), lutein ester (beadlets), mixed tocopherols, calcium carbonate (granular), croscarmellose sodium and microcrystalline cellulose (silicified) are passed through a SWECO separator equipped with a 20 mesh screen directly into a 100 cubic foot PK blender. The mixture is blended for ten minutes. Next, magnesium stearate (Kosher) is passed through a SWECO separator equipped with a 20 mesh screen directly into a 100 cubic foot PK blender. The ingredients are blended for an additional five minutes. The resulting mixture is discharged into totes or supersacks, and compressed into tablets.

Tablet 2

Acerola concentrate, microcrystalline cellulose (silicified) and alpha lipoic acid are passed through a SWECO separator equipped with a 20 mesh screen directly into a 100 cubic foot P.K. blender. The ingredients are blended for ten minutes. Next, the following ingredients are passed through a SWECO separator equipped with a 20 mesh screen directly into the 100 cubic foot PK blender: thiamine mononitrate (97%), riboflavin, niacinamide, biotin trituration (1%), vitamin B12 (1.1%), calcium pantothenate granular, folic acid, pyridoxine HCl (95%), and choline bitartrate. The ingredients are blended for ten minutes. Next, the following items are passed through a SWECO separator equipped with a 20 mesh screen directly into the 100 cubic foot PK blender: beta carotene (beadlets), vitamin D3 (beadlets), yeast (standardized) and vitamin A (acetate). The mixture is blended for an additional ten minutes.

Next, the following ingredients are passed through a SWECO separator equipped with a 20 mesh screen directly into the 100 cubic foot PK blender: ascorbic acid (97%), calcium carbonate (granular), croscarmellose sodium, d-alpha-tocopherol succinate, silicon dioxide (NF fine powder). The mixture is blended for an additional ten minutes.

Next, magnesium stearate (Kosher) is passed through a SWECO separator equipped with a 20 mesh screen directly into the 100 cubic foot PK blender. The mixture is blended for an additional five minutes. The resulting mixture is discharged into totes or supersacks, and compressed into tablets.

Tablet 3

Zinc amino acid chelate, mixed tocopherols and silicon dioxide (NF fine powder) are passed through a SWECO separator equipped with a 20 mesh screen into a 100 cubic foot PK blender. The ingredients are blended for ten minutes. Co-processed alfalfa concentrate/microcrystalline cellulose/calcium carbonate, selenium yeast, microcrystalline cellulose, copper amino acid chelate, manganese amino acid chelate, potassium iodide trituration, chromium amino acid chelate, molybdenum amino acid chelate, brassica dehydrate, watercress dehydrate and croscarmellose sodium are passed through a SWECO separator equipped with a 20 mesh screen directly into the 100 cubic foot PK blender. The ingredients are blended for ten minutes.

Potassium chloride, magnesium oxide (D.C. heavy) and calcium carbonate (granulation) are passed through a SWECO separator equipped with a 20 mesh screen directly into a 100 cubic foot PK blender. The ingredients are blended for ten minutes. Next, magnesium stearate (Kosher) is passed through a SWECO separator equipped with a 20 mesh screen directly into a 100 cubic foot PK blender. The ingredients are blended for an additional ten minutes. Next, magnesium stearate (Kosher) is passed through a SWECO separator equipped with a 20 mesh screen directly into the 100 cubic foot PK blender. The mixture is blended for an additional five minutes. The resulting mixture is discharged into totes or supersacks, and compressed into tablets.

EXAMPLE 3

Clinical testing is being conducted to confirm the efficacy of the supplement of the present invention. It is expected that consumption of the supplement will: correct dietary deficiencies of phytochemicals; improve the amount of antioxidants in the body; decrease free radical damage; increase plasma vitamin, mineral and phytochemical concentrations; and improve plasma and systemic antioxidant capacity, among other things.

The subjects in the study will be healthy men and women, from 18 to 80 years of age, who consume fewer than 12 items found on the Recommended Foods Checklist per week. These subjects are selected after administration of a food frequency questionnaire and application of the Recommended Foods Score (RFS). The RFS consists of 23 foods, 14 of which are fruits and vegetables, that when consumed on a weekly basis have been associated with reduced mortality. This was demonstrated in a cohort study of 42,254 women. Those with a mean RFS of 16.0 (highest quartile) had an all-cause mortality relative risk of 0.69 compared to those with a mean RFS of 6.4 (lowest quartile). It was noted that those in the highest quartile consumed significantly more calories (131%), fiber (200%), Vitamin C (230%), folate (181%), and pro-Vitamin A carotenoids (253%) compared to those in the lowest quartile.

The clinical study encompasses a double-blind (i.e. to subjects and investigators) study of 120 subjects over a six-week period. During the six-week trial, subjects will be assigned to consume three tablets of study product, twice a day with morning and evening meals. The product consumed is either a labeled dose of Double X 2005 or a placebo. The subjects will be tested by taking blood and urine samples and performing the following assays: total polyphenols, plasma ORAC (Oxygen Radical Absorption Capacity), CP450 enzyme induction, cytokinesis block assay, comet assay, bioenergetics assay, urinary bile acids, B6, B12, folate, Vitamin C, homocysteine, alpha and gama tocopherols, beta-carotene, C-reactive protein and urinary 8-epi prostaglandins F2α, which will be tested at baseline, two weeks, four weeks and six weeks into the study. Improvement, and thus, efficacy of the supplement, will be measured based on: plasma concentrations of vitamins, minerals and phytochemicals; plasma and systemic antioxidant capacity; detoxification capacity; cellular energy dynamics; genomic stability; other risk factors and subjective effects.

It is expected that the results of the study will show that following six weeks of supplement consumption, subjects will have significantly increased plasma levels of alpha and gamma tocopherols, B12, B6, folate, Vitamin C, and other antioxidants, which indicates an improvement in the amount of antioxidants in the body and which is associated with a correction of dietary deficiencies in vitamins, nutrients and phytochemicals, and/or a decrease in free radical damage, among other things.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A dietary supplement comprising a fruit ingredient, a vegetable ingredient and an herbal ingredient, the fruit ingredient being pomegranate, present in a dosage range of about 5 to about 500 mg/day, and citrus bioflavonoids, present in a dosage range of about 25 to about 1000 mg/day, the vegetable ingredient being asparagus, present in a dosage range of about 25 to about 1000 mg/day, lutein esters, present in a dosage range of about 0.1 to about 100 mg/day, lycopene, present in a dosage range of about 0.1 to about 100 mg/day, and watercress, present in a dosage range of about 5-500 mg/day, and the herbal ingredient being basil, present in a dosage range of about 25 to about 1000 mg/day, oregano, present in a dosage range of about 25 to about 1000 mg/day, and rosemary, present in a range of about 25 to about 1000 mg/day, wherein the combination of ingredients decreases free radical damage.

2. The dietary supplement of claim 1 further comprising alfalfa, brassica, and kale.

3. The dietary supplement of claim 1 further comprising sage and parsley.

4. The dietary supplement of claim 1 further comprising vitamins and minerals.

5. The dietary supplement of claim 1, wherein the vitamins are chosen from vitamin A, vitamin C, vitamin D, vitamin E, niacin, vitamin $B_6$, vitamin $B_{12}$, folic acid, boitin, and pantothenic acid.

6. The dietary supplement of claim 1 wherein the minerals are chosen from calcium, magnesium, iodine, potassium, copper, zinc, phosphorus, manganese, chromium, selenium, and molybdenum.

7. The dietary supplement of claim 1 wherein the citrus bioflavonoids are in concentrate form and include naringen, hesperidin and narirutin.

8. The dietary supplement of claim 1, wherein the fruit ingredient, the vegetable ingredient and the herbal ingredient are present in a ratio of 3.5:1:1.

* * * * *